United States Patent [19]

Frank

[11] 4,340,041

[45] Jul. 20, 1982

[54] ARTICULATE SPLINT FOR SURGICAL PURPOSES

[75] Inventor: Friedhelm Frank, Karlsruhe-Durlach, Fed. Rep. of Germany

[73] Assignee: Blanc GmbH & Co., Oberderdingen, Fed. Rep. of Germany

[21] Appl. No.: 207,971

[22] PCT Filed: Jan. 24, 1980

[86] PCT No.: PCT/DE80/00008

§ 371 Date: Sep. 24, 1980

§ 102(e) Date: Sep. 17, 1980

[30] Foreign Application Priority Data

Jan. 24, 1979 [DE] Fed. Rep. of Germany ... 7901783[U]

[51] Int. Cl.³ .............................................. A61F 3/00
[52] U.S. Cl. ..................................... 128/80 C; 128/88
[58] Field of Search ................ 128/80 R, 80 C, 80 F, 128/88, 87 R, 83; 3/22

[56] References Cited

U.S. PATENT DOCUMENTS

| 401,933 | 4/1889 | De Camp | 128/88 |
| 489,258 | 1/1893 | Marks | 3/22 |
| 4,144,881 | 3/1979 | Chappell | 128/80 R |
| 4,245,629 | 1/1981 | Cummins | 128/80 C |

FOREIGN PATENT DOCUMENTS

| 1011204 | 5/1977 | Canada | 128/80 C |
| 108422 | 8/1917 | United Kingdom | 128/88 |
| 138783 | 2/1920 | United Kingdom | 128/88 |

*Primary Examiner*—John D. Yasko
*Attorney, Agent, or Firm*—Shenier & O'Connor

[57] ABSTRACT

An articulated splint especially a so-called post-operative knee splint including splint anchor bars enclosed in two plaster casts with a reusable joint member detachably connected to the anchor bars. The two anchor bars are connected to a lock plate of the joint by stubs. A screw extending through apertures in the lock plate adjusts the relative angular position of the stubs and thus of the anchor bars.

7 Claims, 7 Drawing Figures

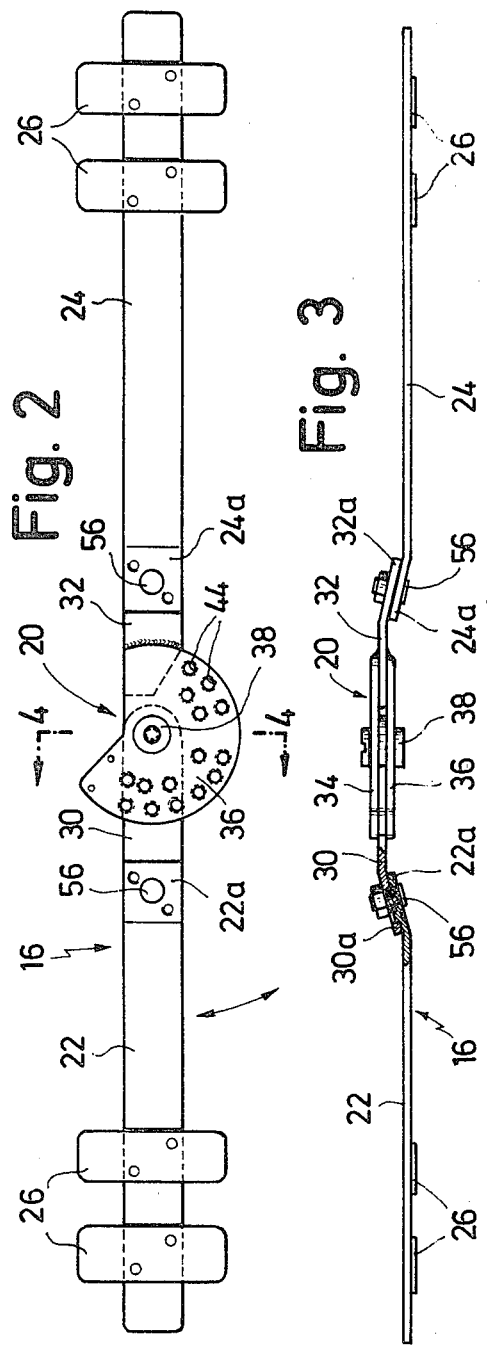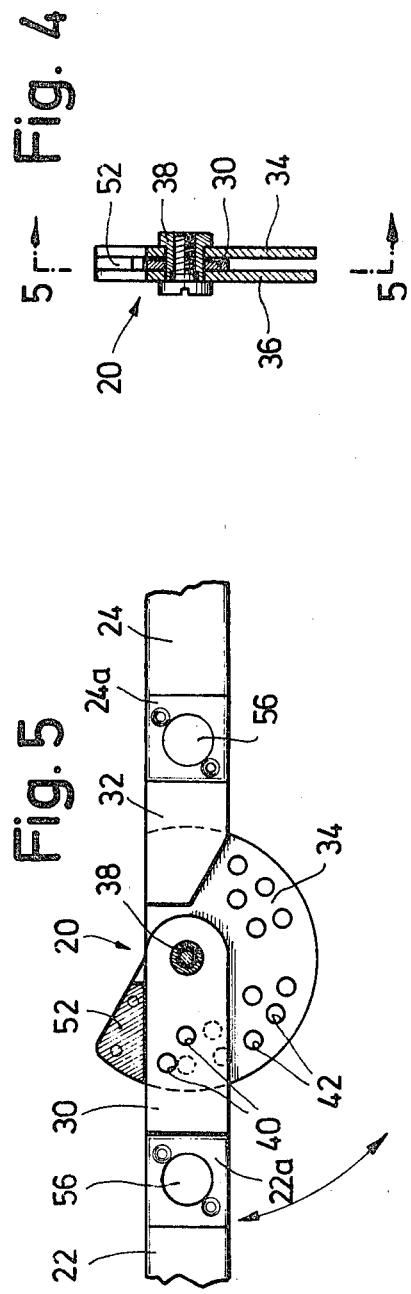

ARTICULATE SPLINT FOR SURGICAL PURPOSES

The invention relates to an articulate splint for surgical purposes, in particular, a knee splint, as used after operations on joints. Known knee splints consist substantially of two anchor bars which are fully or partially embedded in separate plaster of Paris casts on the thigh and the lower part of the leg and are joined to each other by a joint connection. With the anchor bars are set in the plaster of Paris they are arranged such that the joint of the knee splint comes to rest alongside the knee joint so that the axes of rotation of the splint joint and the knee joint register with each other.

In known knee splints, the anchor bars are directly hinged to each other. Since these knee splints consist of stainless steel and are consequently relatively expensive, the anchor bars are often chiselled out of the plaster of Paris after use so that the knee splints can be reused. There is, however, the danger of the knee splints being thereby damaged, more particularly bent, and after they are straightened again, the deformations may result in breakage when the knee splints are used again. Such a breakage can cause injury to the patient. Naturally the same problems arise when articulate splints are used on other joints of the body, such as elbow and finger joints.

The object underlying the invention is therefore to provide a high-quality articulate splint which is less expensive to use than the known joint splints of the above-described kind, even though the anchor bars are not chiselled out of the plaster of Paris on account of the aforementioned risks involved therein. This object is attained in accordance with the invention in that the joint and the anchor bars are constructed as separate parts and the joint is releasably connected to the anchor bars. The invention is based on the consideration that the joint is by far the most expensive part of a stainless steel articulate splint, and it is therefore, above all, the joint that should be made reusable, whereas the anchor bars of relatively simple construction can be thrown away as inexpensive parts with the plaster of Paris, more particularly, the plaster of Paris casts for the thigh and the lower part of the leg.

A particularly simple releasable connection between the joint member and the anchor bars is obtainable by providing the joint with stubs joined to the anchor bars by screw connections. The stubs and the anchor bars can then overlap and be rigidly connected to one another by screws passing therethrough.

It is particularly advantageous for the stubs and the end regions of the anchor bars abutting the stubs to be bent in opposite directions from the plane extending perpendicular to the joint axis, as the joint and the connections between the stubs and the anchor bars which are thicker than the anchor bars themselves, do then not come into contact with the patient's body.

The joint of the known knee splints can only be secured in one angular position. Since the joint member of the articulate splint according to the invention can be reused and can therefore be of a somewhat more complex construction, the articulate splint in accordance with the invention enables fulfillment of a wish which has existed for a long time, namely that of providing the joint member with a detent mechanism which can be secured in several angular positions, so as to permit the patient's joint to be set at rest in various positions.

Further features, details and advantages of the invention are apparent from the enclosed claims and/or the following description and the enclosed drawings of a preferred embodiment of a knee splint constructed in accordance with the invention.

FIG. 2 is a view of one of the two knee splints in the direction of the arrow A in FIG. 1.

FIG. 3 is a plan view of this knee splint, with parts of one anchor bar and one stub broken away.

FIG. 4 is a sectional view of the joint member taken along line 4—4 of FIG. 2.

FIG. 5 is a sectional view of the joint member taken along line 5—5 of FIG. 4.

Figure 1:
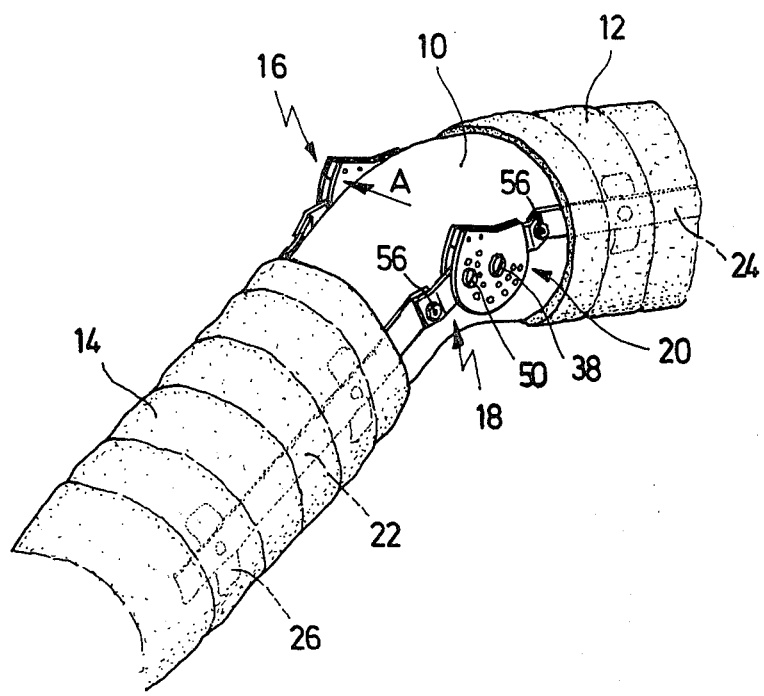
FIG. 1 is a diagrammatic representation of part of a human leg with separate plaster of Paris casts on the thigh and the lower part of the leg, and two knee splints according to the invention.
Figure 6:
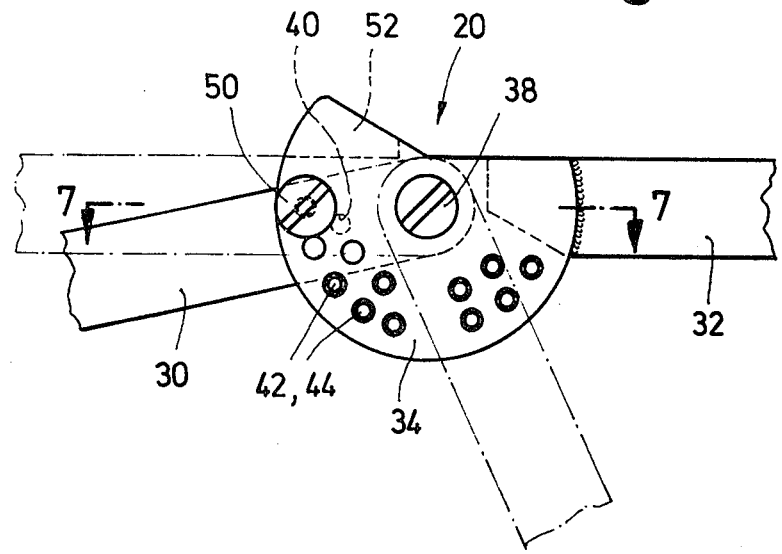
FIG. 6 is a side view of the entire joint member.
Figure 7:
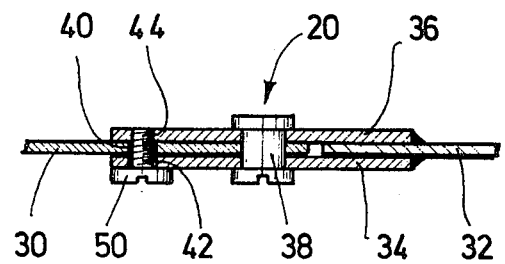
FIG. 7 is a sectional view of the joint member taken along line 7—7 of FIG. 6.

FIG. 1 shows parts of a human leg 10 with plaster of Paris casts 12 and 14 on the thigh and the lower part of the leg, with two so-called knee splints 16 and 18 anchored therein. The construction of these knee splints shall be explained in detail with reference to FIGS. 2 to 7.

Each knee splint comprises a joint member 20 and two anchor bars 22 and 24. All these parts consist of stainless steel. Each of the anchor bars comprises two rivetted crossbars 26 which are likewise covered by the plaster of Paris, as is apparent from FIG. 1.

In accordance with the invention, the ends 22a and 24a facing the joint member 20 are bent outwardly to prevent the joint member 20, which is somewhat thicker, from being pressed against the patient's leg.

The joint member 20 consists substantially of two stubs 30 and 32 and two perforated plates 34 and 36 welded to the stub 32. The stub 30 is hinged to the perforated plates 34, 36 by a joint bolt 38 which can be screwed together, and comprises two apertures 40 which can be made to register with apertures 42 and 44 in the perforated plates 34 and 36. The pattern of the apertures in the perforated plates is such that the two anchor bars 22 and 24 can be secured relatively to each other in the following angular positions: 0°, 10°, 40°, 65°, 90° and 115° (the angle is measured between the straight line defined by the anchor bar in the stretched out state and the angularly positioned anchor bar).

To enable the two anchor bars 22, 24 to be secured relatively to each other, the apertures in the one perforated plate 34 or 36 are in the form of threaded holes, as indicated in FIG. 2, so that one or two screws 50 can be inserted into the apertures in the perforated plates 34 and 36 and in the stub 30 and tightened. Furthermore, there is provided between the perforated plates 34 and 36 a stop member 52 which is rivetted to the two perforated plates 34 and 36 and is abutted by the stub 30 when the anchor bars 22 and 24 assume their stretched position.

The ends 30a and 32a of the stubs 30, 32 abutting the anchor bars are bent inwardly through the same angle as the ends 22a, 24a of the anchor bars outwardly, so that these ends can be placed flat against one another and rigidly joined to one another by several screws 56.

When the plaster of Paris casts are removed from the leg, the screws 56 are simply loosened and the plaster or Paris casts thrown away together with the anchor bars 22 and 24, while the expensive joint member 20 is available for reuse.

I claim:

1. An articulated surgical splint comprising two anchor bars and a joint, said joint including a pair of plates, means securing said plates to each other in spaced parallel relationship, a first stub having a portion received between said plates whereby said first stub is guided thereby, means connecting said first stub to said plates for pivotal movement around an axis perpendicular to the planes of the plates, a second stub secured to said plates, a series of apertures in at least one of said plates and stop means adapted to be set into said apertures for adjusting the relative angular position of said stubs and means for detachably connecting said anchor bars to said stubs.

2. A splint as in claim 1 in which the stubs and the end regions of the anchor bar adjacent to the joint are bent in opposite directions from a plane perpendicular to said axis.

3. A splint as in claim 1 in which said first stub is formed with an aperture adapted to register with one of said plate apertures in response to pivotal movement of said first stub.

4. A splint as in claim 1 in which both plates have a series of apertures, the arrangement being such that the apertures of one plate register with the apertures of the other plate.

5. A splint as in claim 1 in which said means securing said plates to each other comprises a stop adapted to abut said first stub when said first stub is aligned with said second stub.

6. A splint as in claim 4 in which the apertures of one of said plates is in the form of threaded holes and in which said stop means is a screw adapted to be received in said threaded holes.

7. A splint as in claim 1 in which said means connecting said anchor bars to said stubs comprise screws.

* * * * *